United States Patent [19]

Mikulla

[11] 4,312,652
[45] Jan. 26, 1982

[54] SEPARATION SYSTEM

[75] Inventor: Klaus D. Mikulla, Geretsried, Fed. Rep. of Germany

[73] Assignee: Linde Aktiengesellschaft, Wiesbaden, Fed. Rep. of Germany

[21] Appl. No.: 82,452

[22] Filed: Oct. 9, 1979

[30] Foreign Application Priority Data

Oct. 9, 1978 [DE] Fed. Rep. of Germany ....... 2843982

[51] Int. Cl.$^3$ .............................................. F29J 3/02
[52] U.S. Cl. ........................................ 62/29; 62/32; 208/351
[58] Field of Search ............... 208/350, 351, 354, 355; 62/23, 24, 29, 32, 33, 42–44, 40

[56] References Cited

U.S. PATENT DOCUMENTS

| | | | |
|---|---|---|---|
| 3,272,885 | 9/1966 | Davison | 62/24 |
| 3,319,428 | 5/1967 | Isaacson | 208/351 |
| 3,596,472 | 8/1971 | Streich | 62/40 |
| 4,002,042 | 11/1974 | Pryor et al. | 62/40 |

OTHER PUBLICATIONS

"Plant for Production of Ethylene, Propylene, Acetylene, Butadiene, Gasoline & Aromatics", Linde Olefin Symposium, 1978.

Primary Examiner—Frank Sever
Attorney, Agent, or Firm—Millen & White

[57] ABSTRACT

In a process for the separation of a gas mixture comprising a major amount of hydrocarbons, e.g., $C_1$–$C_3$, wherein the gas mixture is liquefied by single or multi-stage partial condensation, where the liquid fractions thus formed are further separated in a first rectifying column, and where following the last stage of partial condensation the resultant gaseous fraction is subjected to rectification in a second rectifying column,
the improvement which comprises the intermediate step of stripping substantially all the most volatile components e.g., $C_1$, from the liquid fractions before the latter are fed into said first rectifying column.

11 Claims, 3 Drawing Figures

4,312,652

SEPARATION SYSTEM

BACKGROUND OF THE INVENTION

This invention relates to a system for the separation of a gas mixture, especially a mixture chiefly of hydrocarbons, and particularly where the gas mixture is subjected to partial condensation, and the resultant liquid is subjected to rectification.

Such a system is used, for example, in the production of ethylene from the gases produced in a plant for the cracking of hydrocarbons. Usually, the cracked gas is compressed and then partly condenced by single or multistage cooling. The fractions thus obtained are conventionally fed into a rectifying column, in which column a sharp separation into two fractions occurs, the first of which contains $C_2$-hydrocarbons and components having a lower boiling point, and the second $C_3$-hydrocarbons and components having a higher boiling point. In order to condense the lower-boiling fraction at the head of the rectifying column, a large amount of cooling to relatively low temperature levels is required, while steam is utilized as reboiler heat at the bottom. Thus, this known method entails the use of a large amount of power.

From DE-OS 26 08 404 [Published Sept. 8, 1977], a method is already known for the separation of gas where power requirements are reduced by dividing the rectification between two separate columns which operate in different temperature ranges and at relatively low differences in temperature between the head and the bottom. An English language equivalent of DE-OS 26 08 404 is U.S. patent application Ser. No. 773,377 of Koening, now abandoned.

SUMMARY OF THE INVENTION

An object of this invention is to provide an improved system for the economic separation of components by a process of the type indicated above, and especially a system having reduced power requirements as compared to DE-OS 26 08 404.

Upon further study of the specification and appended claims, further objects and advantages of this invention will become apparent to those skilled in the art.

To attain these objects, there is provided an improved system comprising stripping the most volatile components from the liquid fractions before the latter are fed into the first rectifying column. By "the most volatile components" are meant components with a boiling point considerably below the boiling point of the heaviest component to be separated from the liquid fractions in the first rectification column.

According to the method given in the invention, the most volatile components in the gas mixture are substantially completely prevented from reaching the first rectifying column. For example, the total amount of the most volatile components, at the head of the first rectification column is less than 5%, especially less than 0.1% by volume. The point of condensation of the mixture to be condensed in the head of the first rectifying column is thus raised to a higher temperature, i.e., the head of the rectifying column can be cooled using higher temperatures, resulting in more economical cooling.

Since in the method according to this invention, in contrast to the known method of DE-OS 26 08 404, no light components arrive in the first rectifying column, this column may also be operated under a lower pressure. This not only leads to a saving in compressor power, but also produces, in addition, a more favorable, i.e. lower reflux ratio in the first rectifying column, since the equilibrium conditions in the gas mixture improve with decreasing pressure.

In an advantageous embodiment of the method according to the invention, the second rectifying column is also provided with a stripping part in its lower section. The gas mixture in the second rectifying column is comprised primarily of volatile components and contains only relatively few heavy components. Since, however, during rectification not only the heavy components are obtained in the bottom but also, at equilibrium, some volatile components, it is an advantage, here also, to strip off the latter, as in the case of the condensates of the preceding partial condensations. A bottom product is thus obtained which, in an advantageous further development of the method, is passed to the first rectifying column at a suitable point for further separation.

It is also an advantage to return the components which have been stripped from the liquid fractions to the gaseous fractions. It is thus possible, in many cases, to do without a special separator for the liquid fractions and to only provide a stripping column, whereas the bottom fraction comprises the condensate freed from the volatile components, and the head fraction contains the remaining components.

A particular advantage of the method according to this invention is shown in a further embodiment where the overhead product of the first rectifying column is completely liquefied, whereupon a part is used as reflux liquid for the first rectifying column, and the remainder, after further cooling, is used as reflux for the second rectifying column. It has been shown that, because only a small amount of reflux liquid is needed in the first rectifying column, the amount of overhead product suffices in many cases to cover the reflux need for the second rectifying column, and a separate condensation stage at the head of the second rectifying column is not needed. This method of operation also has the advantage that the overhead product of the first rectifying column is also fed into the second rectifying column, and fewer demands are made upon the separation in the first rectifying column.

The method according to the invention has an extremely wide field of application. In the separation of the separated gases in an ethylene plant, the method may, for example, be used in a $C_2/C_3$-separation, where $C_1$-hydrocarbons and lower-boiling components are stripped off. Another possible use within an ethylene plant is in a $C_1/C_2$-separation, where hydrogen may be stripped from the condensates as a lower-boiling component. Its use is also possible in the treatment of natural gas. In this case, for example during the partial condensation of $C_2$ to $C_7$-hydrocarbons, the condensates may be rendered free of $C_1$.

BRIEF DESCRIPTION OF THE DRAWINGS

The figures illustrate preferred embodiments for conducting the $C_2/C_3$ separation in the context of an ethylene plant. To this end, three stripping columns are provided before rectification in the schematic flowsheet of FIG. 1, only two being provided in the flowsheet of FIG. 2, and only one stripping column in FIG. 3.

DETAILED DESCRIPTION

Figure 1:
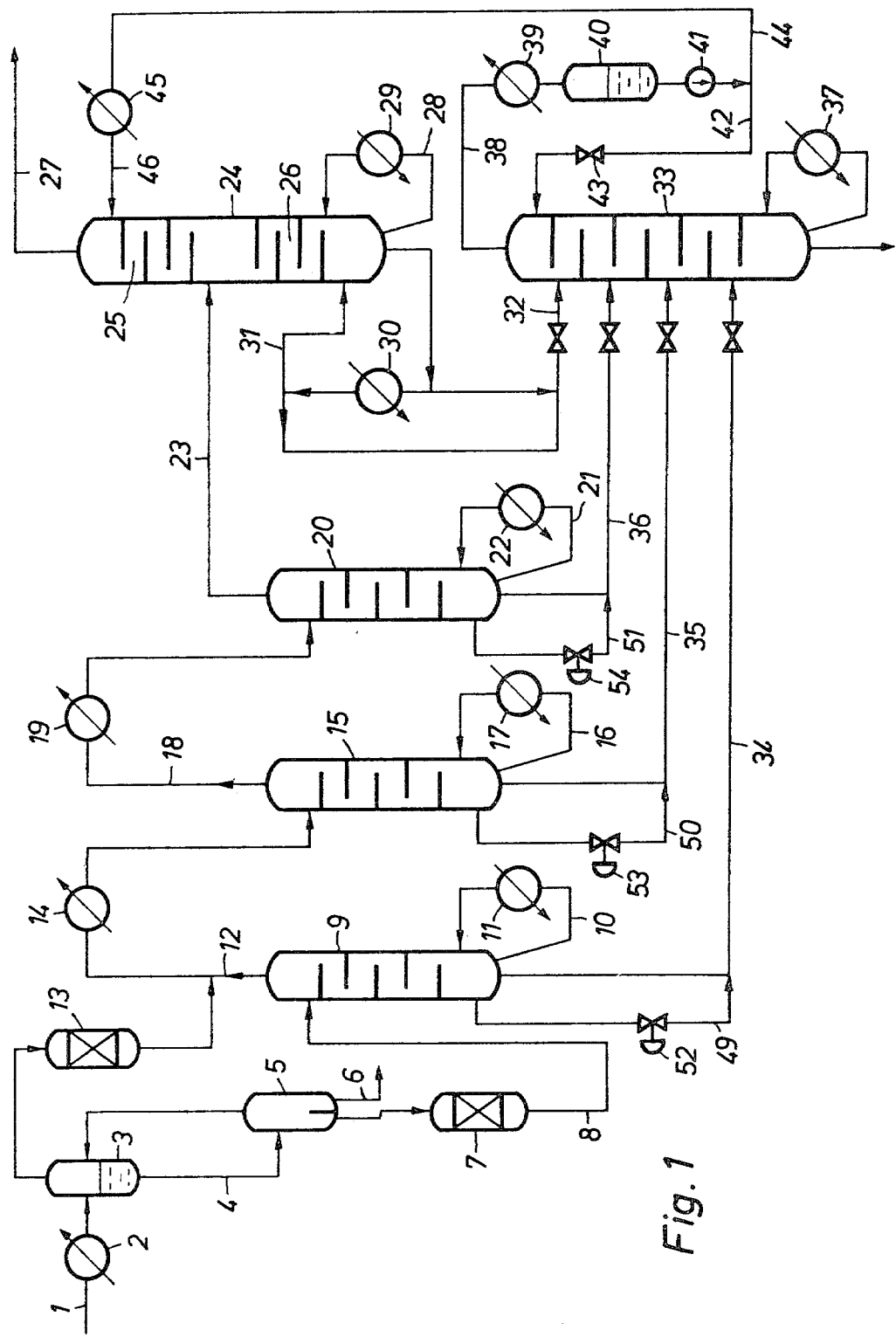

In the method according to FIG. 1, 3789 Nm$^3$/h of condensate, and crude gas amounting to 115,058 Nm$^3$/h, under a pressure of 34.6 bar and at a temperature of 305 K., are fed into the plant. They are cooled to a temperature of 288 K. in heat exchanger 2 which may be of a multi-stage design. The coolants are streams originating from the low-temperature section of the plant which have again been partly heated, e.g., product streams or cooling media of a refrigeration cycle.

During this first cooling, 1.8 Gcal/h of heat is removed from the crude gas. A part of the heavy components in the gas mixture thus condenses, and at equilibrium some light components go into solution. The mixture undergoes a phase separation in separator 3. The liquid phase is first delivered through pipe 4 to a water separator 5 from which the separated water is removed through pipe 6. The remaining water is then removed in dryer 7, whereupon 8337 Nm$^3$/h of condensate is delivered into the upper section of a stripping column 9.

Stripping column 9, having 6 theoretical plates, where the pressure in the head measures 34.1 bar and in the bottom 34.2 bar, is operated at temperatures ranging between 296 K. at the head and 354 K. in the bottom, and operates at a reflux ratio of 3.35 (liquid feed/overhead vapor).

Part of the bottom product is removed through pipe 10, heated in reboiler 11 with low pressure steam and then reintroduced into the column bottom. Heat amounting to 0.72 Gcal/h is required to heat the bottom in order to obtain 6485 Nm$^3$/h of methane-free bottom product and 1852 Nm$^3$/h overhead product.

The overhead product is removed through pipe 12 and is combined with the gaseous fraction from separator 3 after having been dried in dryer 13. Cooling to 258 K. by the product gases (e.g., hydrogen, methane, ethane, ethylene) and by propane refrigerant then occurs in heat exchanger 14, a part of the gas mixture again condensing. During this heat exchange, 3.6 Gcal/h of heat is removed from the gas mixture.

The mixture is then fed into a second stripping column 15 where a $C_1$-free condensate is again separated as a bottom product. To achieve this, the column, operating under a pressure of 33.7 bar at the head and 33.8 bar at the bottom, is equipped with nine theoretical plates and operated at temperatures of 264 K. at the head and 311 K. at the bottom. The reflux ratio is 3.61.

Through pipe 16, a part of the bottom product is delivered to a reboiler 17 by means of which 0.93 Gcal/h of heat is provided to the column bottom. 11,969 Nm$^3$/h of $C_1$-free product is formed in the bottom, 3,420 Nm$^3$/h of light components being stripped from the condensate of the second cooling stage. Because of the low temperature level of 311 K. at the bottom of stripping column 15, heating of reboiler 17 may be done with wash water used in the quenching of the hot cracked gases. It is obtained at a temperature of about 350 K. and can no longer be used to make steam. The use of this heat potential, which generally is discharged unused into the environment as waste heat, considerably improves the economy of the invention. The details of the production of the hot wash water is conventional and described in the information "Plant for production of ethylene, propylene, acetylene, butadiene, gasoline and aromatics" of the Linde AG. A detailed process scheme is shown in "Linde Olefins Symposium", Munich 1978, page U41.

The remaining gaseous components of the gas mixture subsequently arrive through conduit 18 at a third condensation stage, where heat amounting to 2.5 Gcal/h is removed from the gas mixture. The gas mixture is thereby cooled in heat exchanger 19 to a temperature of 239 K. It is then delivered to a third stripping column 20, where a $C_1$-free condensate is again separated at the bottom. Column 20 operates under a pressure of 33.6 bar at the head and 33.7 bar at the bottom. It contains seven theoretical plates and is operated at a reflux ratio of 2.36 at temperatures ranging between 254 K. at the head and 292 K. at the bottom.

Just as in columns 9 and 15, here, too, a part of the bottom product is fed via pipe 21 through a reboiler 22, where 1.0 Gcal/h of heat is absorbed and 10,352 Nm$^3$/h of light components free of $C_1$ is obtained. 5,421 Nm$^3$/h of light components is thereby separated from the condensate of the third cooling stage.

Both heat exchanger 22 and heat exchanger 17 are heated with cheap waste heat from the quenching wash water.

The non-condensed components of the gas mixture, only contained 2.4 Mole-% of $C_3$-hydrocarbons and heavier components, are delivered through pipe 23 into rectifying column 24 (2nd rectifying column). This rectifying column 24 is equipped with an enriching part 25 in the upper section, and with a stripping part 26 in the lower section, between which the gas mixture is introduced. In enriching part 25, the components still remaining in the gas mixture which are heavier than $C_2$-hydrocarbons, are separated, so that a mixture of $C_2$-hydrocarbons and lighter components may be removed as overhead product through pipe 27, which mixture contains virtually no more $C_3$-hydrocarbons and heavier components.

The $C_1$-hydrocarbon and still lower-boiling components, which have gone into solution during rectification, are again stripped in stripping part 26. This involves again heating a part of the bottom product and returning it to the bottom, similarly to columns 9, 15 and 20. A part of the bottom product is delivered via pipe 28 through a heat exchanger 29 which also may be heated with wash water, another part of the bottom product being furthermore heated in a heat exchanger 30 and returned through pipe 31. This heat exchanger 30 may be heated with crude gas and may, for example, for part of heat exchanger 2. In addition, the bottom of rectifying column 24 may also be heated with coolants such a propylene, of a suitable temperature.

Rectifying column 24 is operated under a pressure of 33.4 bar at the head and 33.6 bar at the bottom. It is equipped with thirteen theoretical plates and operates at temperatures ranging between 234 K. at the head and 286 K. at the bottom. At a reflux ratio of 0.20, 7,775 Nm$^3$/h of $C_1$-free condensate is thereby obtained, 100,858 Nm$^3$/h of $C_{3+}$-free gas mixture being removed as overhead product. The bottom of rectifying column 24 is heated at 1.0 Gcal/h.

The $C_1$-free bottom product removed from rectifying column 24 is expanded and delivered through pipe 32 to the upper section of rectifying column 33. In addition, the $C_1$-free bottom products of columns 9, 15 and 20 are separately introduced, after expansion, into rectifying column 33 through pipes 34, 35 and 36, respectively. The condensate containing the heaviest components from column 9 is introduced into rectifying column 33 at a lower point than are the lighter condensates from columns 15 and 20, the suitable points of introduction being determined from the equilibrium present in rectifying column 33 and from the composition of the condensates in pipes 32, 34, 35 and 36. In order to be able to conduct the separation in rectifying column 33 under the most favorable conditions, a slight excess of vapor is produced in the bottom of stripping columns 9, 15 and 20, which vapor is extracted through pipes 49, 50 and 51, respectively and fed into the rectifying column together with the condensates. The amount of vapor introduced may be controlled by valves 52, 53, 54, and on a weight basis, preferably comprises about 5 to 50% of the total fluid in conduits 34, 35 and 36.

Since rectifying column 33 is charged with $C_2$-hydrocarbons as the lightest component, the separation into a $C_2$- and a $C_{3+}$- fraction may be carried out with little consumption of power. The separation occurs at a column pressure of 26 bar at the head and of 26.3 bar at the bottom, thirty-one theoretical plates being provided, and temperatures ranging between 260 K. at the head and 360 K. at the bottom being maintained. In order to maintain the bottom temperature, 3.6 Gcal/h are delivered to heat exchanger 37. At a reflux ratio of 0.46, 17,632 Nm$^3$/h of a $C_2$-free fraction are obtained as bottom product, 18,948 Nm$^3$/h of overhead product being removed as a virtually $C_{3+}$-free fraction of $C_2$ through pipe 38.

This overhead product is completely liquefied in heat exchanger 39 using a coolant at 253 K. 3.2 Gcal/h being given off to the coolant. Propylene, for example, may be used as a coolant. The condensate is collected in container 40.

The condensed overhead product is then pressurized by means of pump 41 to the pressure prevailing in rectifying column 24. Via pipe 42, a part (e.g. 30 to 60%) of the condensate is then diverted, to be reintroduced as reflux liquid into rectifying column 33 after expansion at 43. The remaining part of the condensate is delivered via pipe 44 through a heat exchanger 45 where it is supercooled to 233 K., and where 0.34 Gcal/h of heat is transferred to a coolant, such as propylene. The supercooled liquid is then delivered as reflux liquid via pipe 46 to rectifying column 24.

Figure 2:
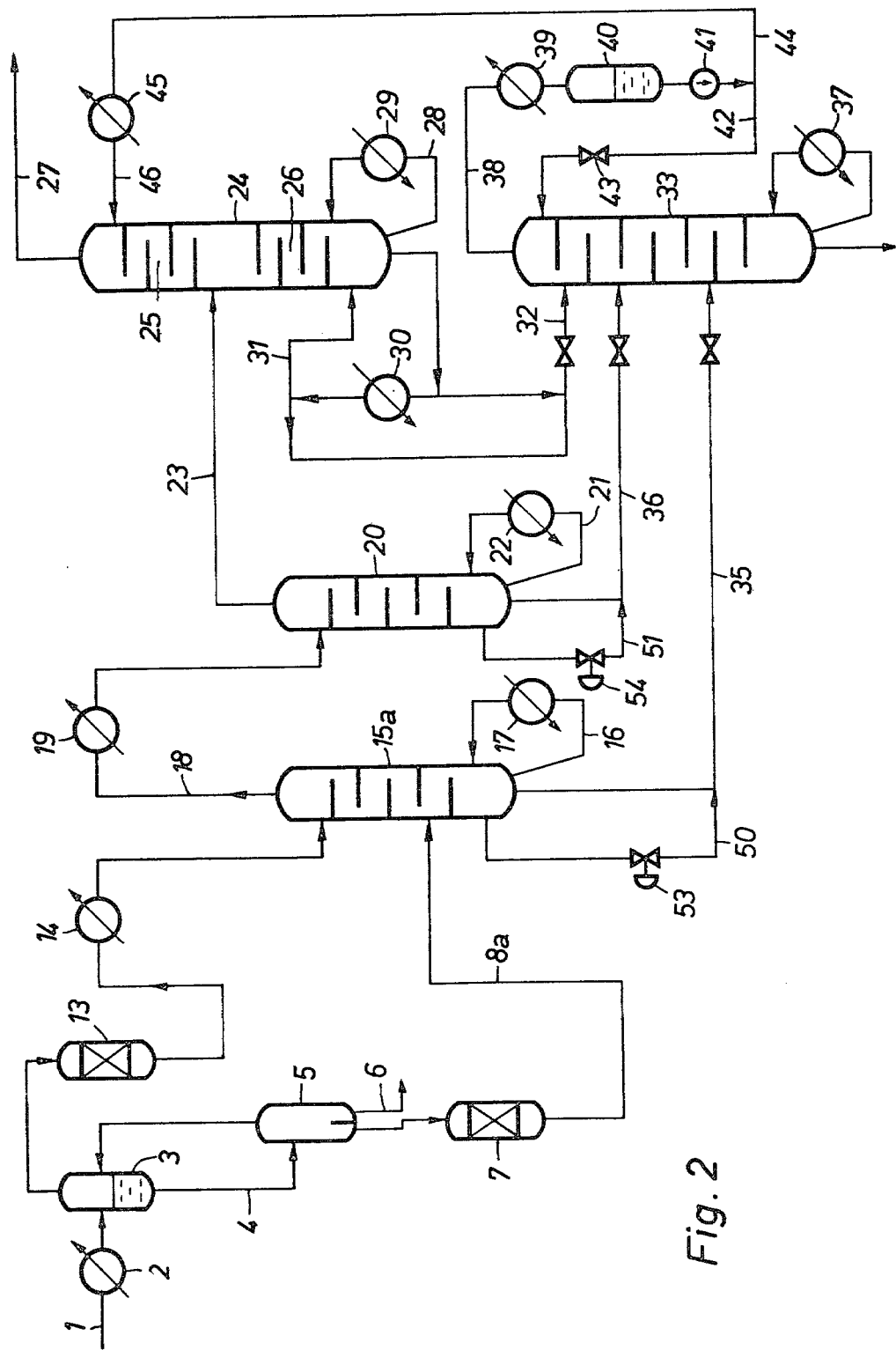

The method illustrated in FIG. 2 differs essentially from the one given in FIG. 1 by the fact that here only two stripping columns 15a and 20 are provided instead of three. Here the condensate emerging from dryer 7 is not delivered into its own stripping column, but arrives through pipe 8a in the central section of stripping column 15a, whose upper section is fed with the gas mixture which has been partly condensed in heat exchanger 14 through the removal of 3.5 Gcal/h. In this method of operation, column 15a is operated under different conditions than in the example given in FIG. 1. It is now equipped with eleven theoretical plates and operates at temperatures ranging between 365 K. at the head and 323 K. at the bottom. 18,426 Nm$^3$/h of $C_1$-free condensate is thereby removed from the bottom, and 4,850 Nm$^3$/h of light components is stripped from the introduced condensate. 1.5 Gcal every hour from wash water is provided to the bottom heater through heat exchanger 17.

In heat exchanger 19, 1.7 Gcal of heat is removed every hour from the overhead product from column 15a, this overhead product cooling down to 254 K. and partly condensing. In stripping column 20, a $C_1$-free condensate and a light overhead product are obtained from it. Tho this end, this column is provided with eleven theoretical plates and operates at temperatures ranging between 254 K. at the head and 292 K. at the bottom. 10,434 Nm$^3$/h of $C_1$-free condensate is obtained as bottom product, and 5,460 Nm$^3$/h of light components is separated from the introduced condensate. It is therefore necessary to provide 1.0 Gcal of heat in the bottom every hour, through exchanger 22, which heat may again be obtained by means of wash water.

This method of operation has the advantage that none of the columns needs to be heated at the bottom with relatively expensive steam, but that the use of wash water is possible in both remaining columns.

Figure 3:
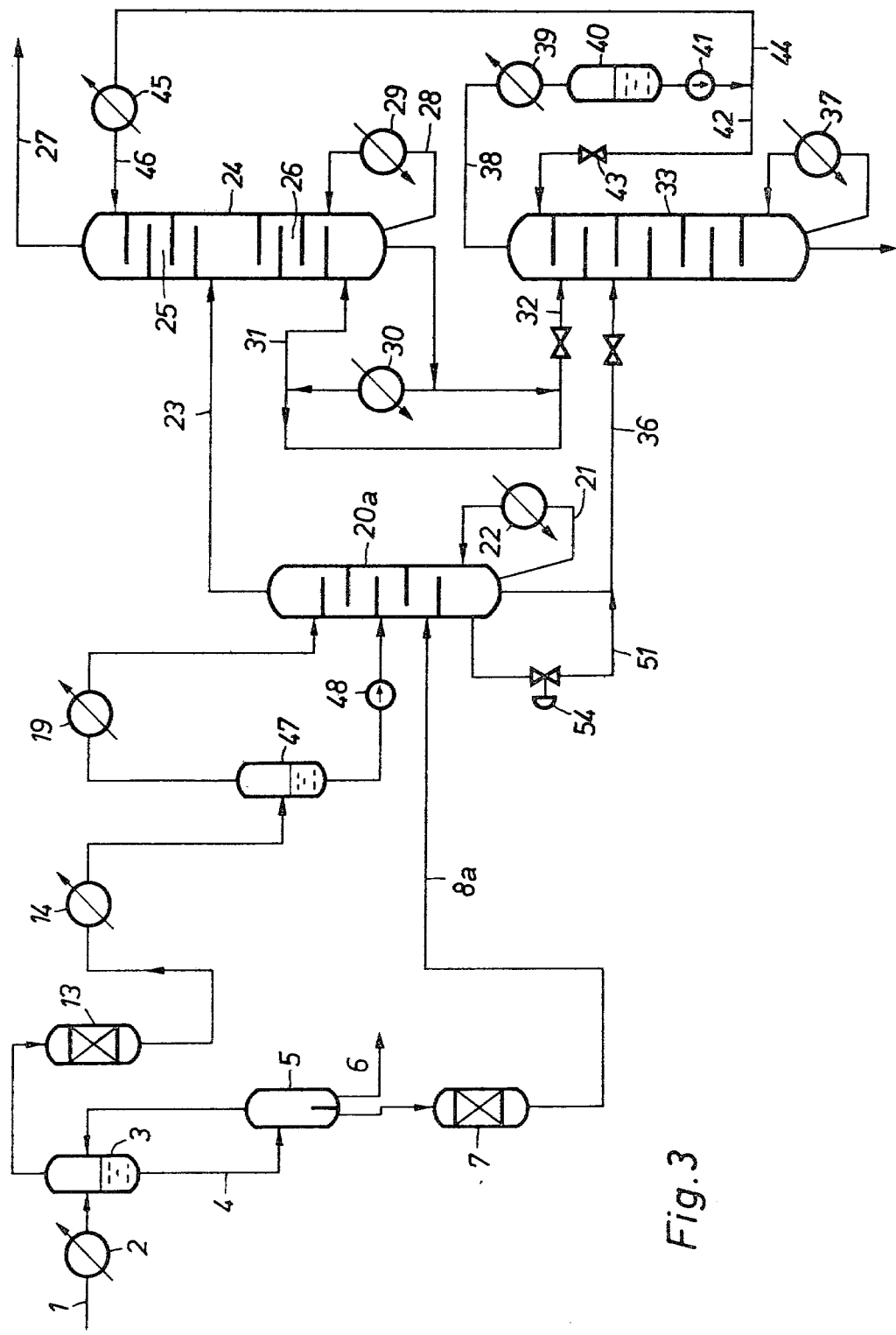

Finally, in the method shown in FIG. 3, only one stripping column 20a is used. In contrast to the method shown in FIG. 2, stripping column 15a has been replaced by a separator 47. The condensate separated in this separator is delivered at a suitable point via a pump 48 to stripping column 20a. The gaseous fraction from separator 47, after further cooling in heat exchanger 19 where 1.5 Gcal/h of heat is removed, is delivered to stripping column 20a. Furthermore, the condensate obtained in the first condensation stage is delivered through pipe 8a to a lower section of stripping column 20a.

In this embodiment, the stripping column is equipped with eleven theoretical plates and is operated under a pressure of 33.6 bar at the head and 33.7 bar at the bottom. The head temperature is 250 K., the bottom temperature 310 K. At a reflux ratio of 1.54, 28,876 Nm$^3$/h of $C_{1-}$-free bottom product is produced, which is delivered through pipe 36 to rectifying column 33. Heat exchanger 22 is heated at 2.2 Gcal/h. Of the condensates delivered to stripping column 20a, 8,995 Nm$^3$/h of gaseous components is separated and delivered together with the non-condensed gas mixture through pipe 23 to rectifying column 24.

In this method of operation, it is necessary to heat the bottom at 4.3 Gcal/h to separate the $C_2$ hydrocarbons in rectifying column 33. For the condensation of the overhead product, 3.7 Gcal/h are required in heat exchanger 39.

All examples were based on a gas mixture having the following composition (anhydrous):

| | |
|---|---|
| $H_2$ | 1.30% by weight |
| CO | 0.13% by weight |
| $CH_4$ | 24.39% by weight |
| $C_2H_2$ | 0.62% by weight |
| $C_2H_4$ | 37.67% by weight |
| $C_2H_6$ | 8.42% by weight |
| $C_3H_4$ | 0.90% by weight |
| $C_3H_6$ | 14.98% by weight |
| $C_3H_8$ | 0.47% by weight |
| $C_{4+}$ | 11.12% by weight |

The condensed portion in question has the following composition:

| | |
|---|---|
| $H_2$ | 0.03% by weight |
| $CH_4$ | 2.14% by weight |
| $C_2H_2$ | 0.20% by weight |
| $C_2H_4$ | 10.34% by weight |
| $C_2H_6$ | 3.01% by weight |
| $C_3H_4$ | 0.80% by weight |
| $C_3H_6$ | 13.27% by weight |
| $C_3H_8$ | 0.48% by weight |
| $C_{4+}$ | 69.73% by weight |

The water content of the gas is 0.11% by weight, that of the condensed part 1.54% by weight.

When a $C_1$- or methane-free condensate is referred to, the condensate is not only free of methane, but of lower boiling gases as well.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for the separation of a gas mixture comprising a major amount of hydrocarbons wherein the gas mixture is liquefied by single or multi-stage partial condensation in one or more heat exchangers at least partially cooled by external refrigerant, where the liquid fractions thus formed are further separated in a first rectifying column, and where following the last stage of partial condensation the resultant gaseous fraction is subjected to rectification in a second rectifying column, each of said rectification columns having an enriching zone and a stripping zone, and wherein said gas mixture is derived from a source other than said rectification columns, the improvement which comprises the intermediate step of stripping the most volatile components from the liquid fractions before the latter are fed into said first rectifying column, so as to substantially decrease the cooling requirements of said first rectifying column, said stripping being conducted in a stripping column separated from said rectification columns.

2. A process according to claim 1, where in the enriching zone of the second rectification column, heavier components are separated from the gaseous fraction and where in the stripping zone the most volatile components having gone into solution are again at least partly stripped.

3. A process according to claim 2, wherein the bottom product of the second rectifying column is delivered to the first rectifying column for further separation.

4. A process according to claim 3, wherein the stripped components of the liquid fractions or of the bottom product of the second rectifying column respectively are reintroduced into the respective gaseous fractions.

5. A process according to claim 2 for the separation of a hydrocarbon mixture into a $C_2$ and a $C_{3+}$ fraction, wherein the volatile components lighter than $C_2$-hydrocarbons are removed from the liquid fractions and the $C_2$-hydrocarbons are removed from the first rectifying column, and in the enriching zone of the second rectifying column the volatile components heavier than $C_2$-hydrocarbons are separated from the gaseous fraction.

6. A process according to claim 2 for the separation of a hydrocarbon mixture into a $C_1$ and $C_{2+}$ fraction, wherein the volatile components lighter than $C_1$-hydrocarbons are removed from the liquid fractions and the $C_1$-hydrocarbons are removed in the first rectifying column, and that in the enriching part of the second rectifying column the volatile components heavier than $C_1$-hydrocarbons are separated from the gaseous fraction.

7. A process according to claim 1, wherein volatile components in the first rectification column still in solution are separated from the liquid fractions, and overhead product of the first rectifying column is liquefied and delivered partly to the first rectifying column and partly to the enriching zone of the second rectifying column as reflux liquid.

8. A process according to claim 1 for the separation of a hydrocarbon mixture into a $C_2$ and a $C_{3+}$ fraction, wherein the volatile components lighter than $C_2$-hydrocarbons are removed from the liquid fractions and the $C_2$-hydrocarbons are removed in the first rectifying column.

9. A process according to claim 8, wherein the second rectification column is heated at least partly by hot wash water as reboiler heat transfer fluid.

10. A process according to claim 8, wherein the removal of the components lighter than $C_2$-hydrocarbons occurs at least partly by heating with hot wash water as reboiler heat transfer fluid.

11. A process according to claim 1 for the separation of a hydrocarbon mixture into a $C_1$ and a $C_{2+}$ fraction, wherein the volatile components lighter than $C_1$-hydrocarbons are removed from the liquid fractions and the $C_1$-hydrocarbons are removed in the first rectifying column.

* * * * *